(12) United States Patent
Zinser, Jr. et al.

(10) Patent No.: US 7,676,261 B2
(45) Date of Patent: *Mar. 9, 2010

(54) METHOD AND SYSTEM FOR ENHANCING PACE PULSES

(75) Inventors: Richard Louis Zinser, Jr., Niskayuna, NY (US); Emad Andarawis Andarawis, Ballston Lake, NY (US); Jeffrey Michael Ashe, Gloversville, NY (US); Nicholas George Richard, Lakeville, MA (US)

(73) Assignee: General Electric Company, Niskayuna, NY (US)

( * ) Notice: Subject to any disclaimer, the term of this patent is extended or adjusted under 35 U.S.C. 154(b) by 1554 days.

This patent is subject to a terminal disclaimer.

(21) Appl. No.: 10/954,738

(22) Filed: Sep. 30, 2004

(65) Prior Publication Data

US 2006/0069321 A1    Mar. 30, 2006

(51) Int. Cl.
*A61B 5/04* (2006.01)

(52) U.S. Cl. .................................... 600/510

(58) Field of Classification Search ......... 600/508–510; 375/350; 327/227, 229; 128/898; 607/42
See application file for complete search history.

(56) References Cited

U.S. PATENT DOCUMENTS 3,699,360 A * 10/1972 Ragsdale ..................... 327/227
5,802,118 A *  9/1998 Bliss et al. ................... 375/350

OTHER PUBLICATIONS

Lensu, T.; Vehvilainen, M.; Tenhunen, H.; Neuvo, Y.; "Detection of Rectangular Pulses Using Median Based Prefiltering"; Systems Engineering, 1990., IEEE International Conference on , Aug. 9-11, 1990; pp. 224-227.

* cited by examiner

*Primary Examiner*—George Manuel
(74) *Attorney, Agent, or Firm*—Patrick K. Patnode

(57) ABSTRACT

A method for enhancing pace pulses is presented. The method includes providing a set of digital electrocardiogram data comprising a plurality of pulses, wherein each pulse is of a generally constant width. Furthermore, the method includes differentiating the plurality of pulses to generate a plurality of pairs of differentiated pulses, wherein each pair of differentiated pulses is separated by the generally constant width of the corresponding pulse. In addition, the method includes enhancing the plurality of pairs of differentiated pulses. Systems and computer-readable medium that afford functionality of the type defined by this method are also provided by the present technique.

66 Claims, 5 Drawing Sheets

METHOD AND SYSTEM FOR ENHANCING PACE PULSES

BACKGROUND

The invention relates generally to electrocardiogram systems, and more specifically to the enhancement and detection of pace pulses in electrocardiogram data.

A pacemaker is an electronic device used to treat patients who have symptoms caused by abnormally slow heartbeats. The pacemaker keeps track of the patient's heartbeat. For instance, if the patient's heart is beating too slowly, the pacemaker may generate electrical signals similar to that of the heart's natural signals, thereby causing the heart to beat faster. The purpose of the pacemaker is to maintain heartbeats in order to ensure that adequate oxygen and nutrients are delivered through the blood to the organs of the body.

An electrocardiogram (ECG or EKG) is generally, though not always, a non-invasive technique that is used to reflect underlying heart conditions by measuring the electrical activity of the heart. By positioning leads on or in the body in standardized locations, information about many heart conditions may be learned by looking for characteristic patterns in the ECG waveforms.

In order to efficiently evaluate ECG results, the diagnostician must know if the heart is being actively paced. However, due to rapid advancement in technology, the modern pacemakers are increasingly using lower voltages and power levels than those previously employed. Hence, the output from the newer pacemakers is often not visible on a conventional ECG machine.

It is becoming increasingly difficult to efficiently detect pace pulses in an adverse clinical ECG environment. Furthermore, the detection of pace pulses may be complicated by the presence of spurious signals such as impulsive noise and programmer pulses. Therefore, it may be desirable to develop a robust technique to detect pace pulses in raw ECG data.

BRIEF DESCRIPTION

Briefly, in accordance with an exemplary embodiment of the present technique, a method for enhancing pace pulses is presented. The method includes providing a set of digital electrocardiogram data comprising a plurality of pulses, wherein each pulse is of a generally constant width. Furthermore, the method includes differentiating the plurality of pulses to generate a plurality of pairs of differentiated pulses, wherein each pair of differentiated pulses is separated by the generally constant width of the corresponding pulse. In addition, the method includes enhancing the plurality of pairs of differentiated pulses. Systems and computer-readable medium that afford functionality of the type defined by this method are also provided by the present technique.

According to a further embodiment of the present technique, a method for enhancing pace pulses is presented. The method includes providing digital ECG data comprising a plurality of pace pulses. The plurality of pace pulses in the digital ECG data is attenuated to generate a filtered set of the digital ECG data. The filtered set is subtracted from a corresponding synchronized unfiltered set of digital ECG data to generate an enhanced set of digital ECG data. Systems and computer-readable medium that afford functionality of the type defined by this method are also provided by the present technique.

In accordance with another embodiment of the present technique, a method for combining signals is presented. The method includes providing a plurality of sets of digital ECG data. A signal strength of the plurality of sets of digital ECG data is measured and the plurality of sets of digital ECG data is combined based on the signal strength to generate a combined set of digital ECG data. Systems and computer-readable medium that afford functionality of the type defined by this method are also provided by the present technique.

DRAWINGS

DETAILED DESCRIPTION

Modern pacemakers are increasingly employing significantly lower voltages and power levels than those previously employed. Consequently, the output from these new pacemakers may not be visible in electrocardiogram data using existing techniques. It may therefore be desirable to develop techniques that enable the efficient detection of these high-bandwidth, low-power pace pulses in electrocardiogram data so that a diagnostician may be made aware that a heart is being actively paced. The techniques discussed herein address some or all of these issues.

Figure 1:
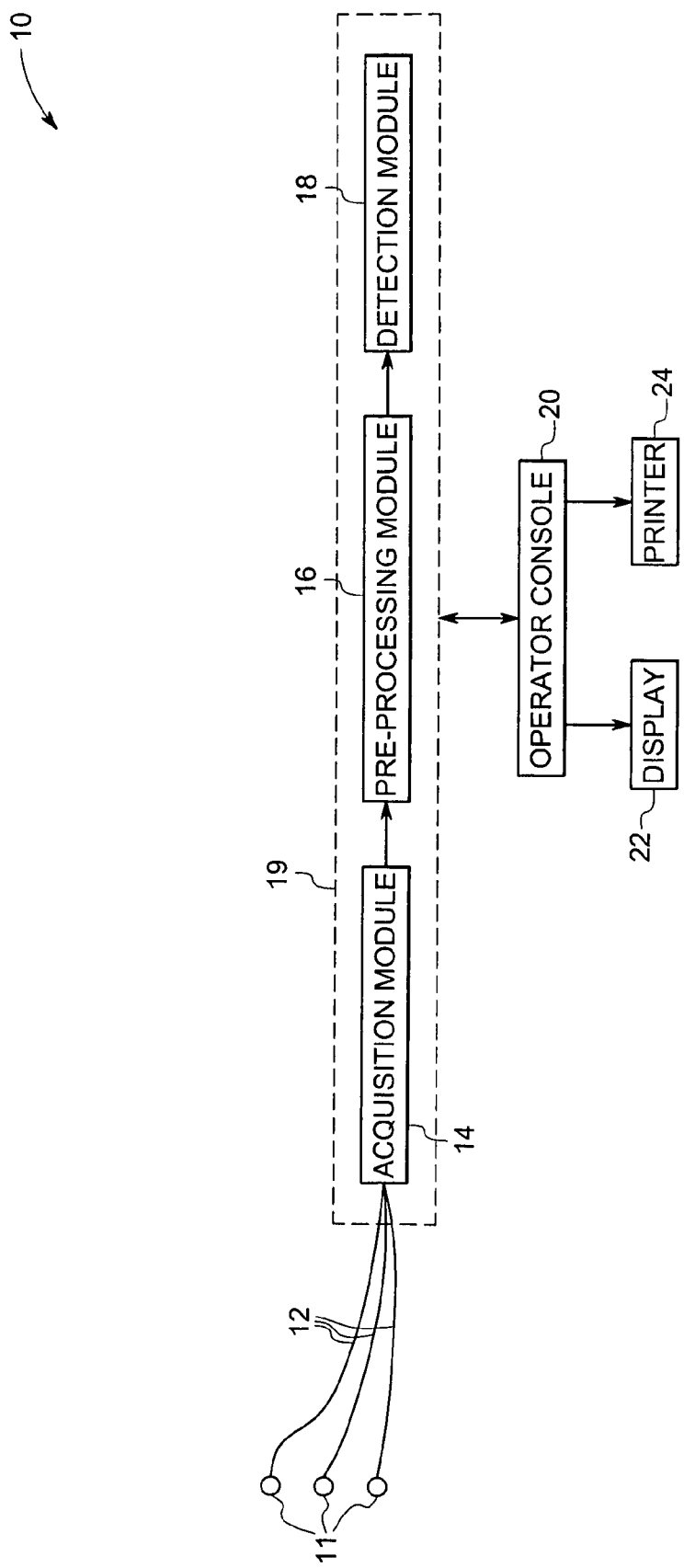
FIG. 1 is a block diagram of a system for enhancing pace pulses in electrocardiogram data, in accordance with one aspect of the present technique.

Referring to FIG. 1, a block diagram depicting an electrocardiogram (ECG) system 10 that detects pace pulses in accordance with the present technique is illustrated. The ECG system 10 may include a plurality of electrodes 11 configured to be disposed on or in a patient. Also, as shown as in FIG. 1, a plurality of electrode wires 12 facilitates the acquisition of ECG data from the electrodes 11 by an acquisition module 14. While wires 12 may be used in some exemplary implementations, other exemplary implementations may use wireless techniques, such as infrared or radio frequency transmission, for providing ECG data from the electrodes 11 to the acquisition module 14. In addition, while electrodes 11 and wires 12 may be used to directly acquire ECG data from a patient, the acquisition module 14 may instead acquire stored ECG data from an archive site or data storage facility. The acquisition module 14 may include circuitry to digitize the ECG data, if needed, or such digitization may occur in another downstream module.

The ECG system 10 may include a pre-processing module 16 that may be configured to process the ECG data acquired by the acquisition module 14. The pre-processing module 16 may facilitate processing the ECG data prior to the detection of pace pulses, where the processing may include steps such as, but not limited to, differentiating, filtering and applying a non-linear pulse signature enhancement. For example, the pre-processing module 16 may include general or specialized circuitry for processing and/or differentiating ECG signals as described herein. For example, in one embodiment, the pre-processing module 16 may apply enhancement algorithms to one or more sets of ECG data. In one such embodiment, the enhancement algorithms may be based on non-linear processing principles, where non-linearity may be defined as a violation of the superposition principle or as a distortion of the signal such that the output signal amplitude does not scale linearly with the input amplitude.

Furthermore, the ECG system 10 may include a detection module 18 that may be configured to detect pace pulses in the ECG data. The various modules and processing components, such as acquisition module 14, pre-processing module 16 and the detection module 18 may constitute an acquisition and detection system 19 that may be accessed and/or operated via an operator console 20. The operator console 20 may also be employed to facilitate the display of detected pace pulses, such as on a display 22 and/or a printer 24. For example, an operator may use the operator console 20 to designate the manner in which detected pace pulses are displayed, such as on a separate trace from the corresponding ECG data or superimposed on the corresponding ECG data.

Figure 2:
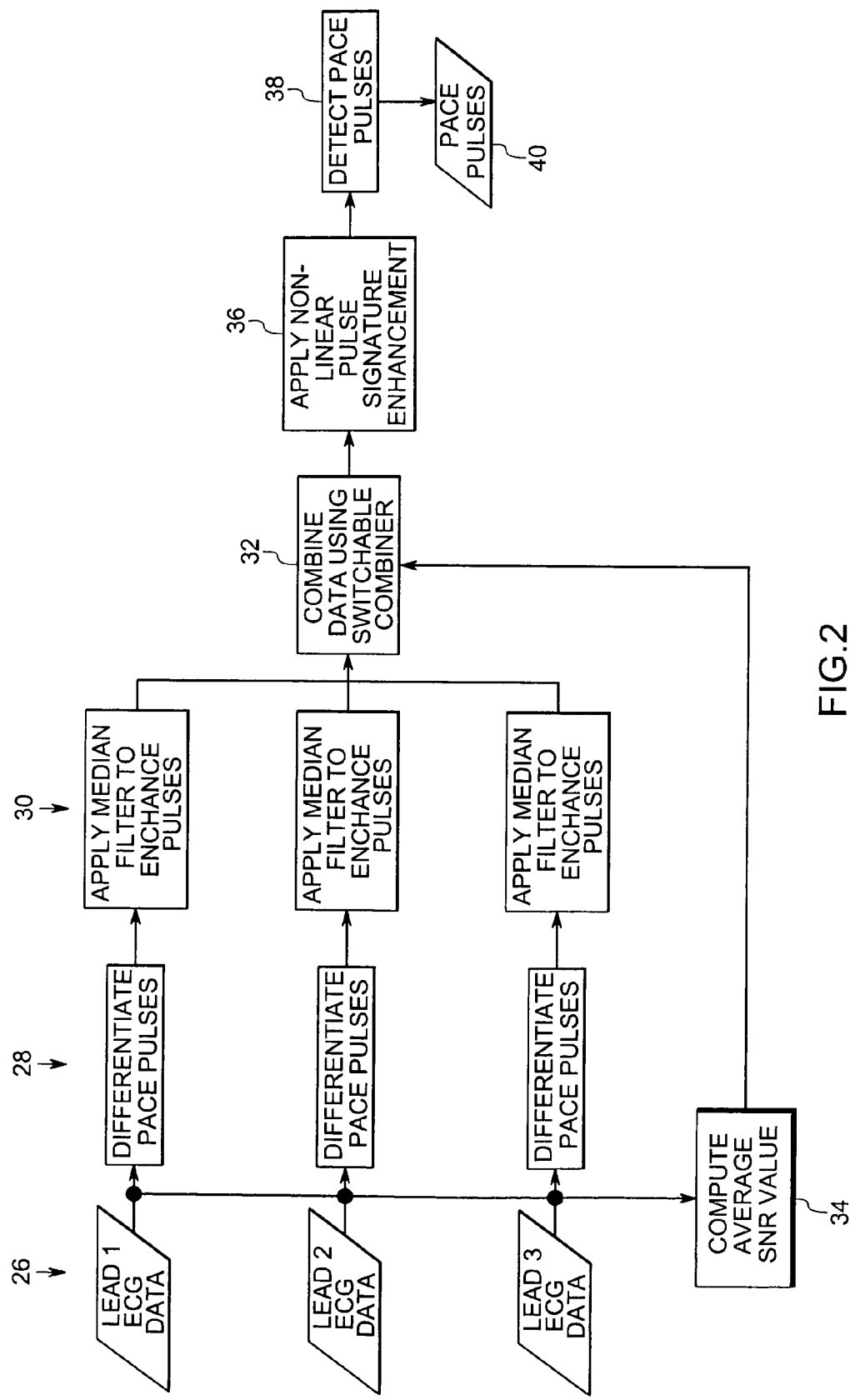
FIG. 2 depicts a flowchart illustrating steps for enhancing pace pulses in electrocardiogram data, in accordance with one aspect of the present technique.

Referring now to FIG. 2, a flowchart depicting steps for enhancing pace pulses in ECG data, in accordance with the present technique, is illustrated. In the example depicted by FIG. 2, a set of ECG data 26 is acquired from each respective electrode wire 12, such as may be connected to a respective electrode 11 disposed on or in a patient. Although FIG. 2 depicts a system that uses 3 ECG data sets, one of ordinary skill in the art will appreciate that the depicted method may be generally applicable to ECG systems employing two or more data sets. The acquired sets of ECG data 26 may include a plurality of pulses, such as pace pulses generated by a pacemaker, where each of the plurality of pace pulses is of a generally constant width.

Referring again to FIG. 2, the ECG data 26 may be processed via a differentiator at step 28. More specifically, the ECG data 26 may be processed via the differentiator to generate a plurality of pairs of differentiated pulses. Where each pair of differentiated pulses is separated by the generally constant width of the corresponding pulse. Furthermore, as depicted in step 30 the ECG data may be processed to enhance the pace pulses that may be present in the ECG data 26. For example, the ECG data 26 may be processed via a filter to enhance the pace pulses that may be present in the ECG data 26. Additionally, the ECG data sets 26 may be combined via a switchable combiner, as depicted in step 32, to generate a single combined signal that may be analyzed to detect pace pulses.

In accordance with one aspect of the embodiment depicted in FIG. 2, the ECG data sets 26 may be processed to enhance the pace pulses that may be present in the ECG data sets 26 while attenuating spurious signals, such as, but not limited to, extraneous noise and non-pacemaker pulses. In this embodiment, the enhancement of pace pulses and attenuation of non-pace pulses may be based on an interval or spacing, such as the generally constant width of the pace pulses. In one embodiment, the generally constant width of the pace pulses may include an average pulse width.

Similarly, in accordance with another aspect of the embodiment depicted in FIG. 2, the ECG data sets 26 may be combined based upon a signal-to-noise ratio (SNR) associated with the ECG data sets 26 that may be computed by a SNR detector 34. Furthermore, the combined signal may be processed via a non-linear pulse signature enhancer, as depicted in step 36, to enhance the pace pulses that may be present in the combined signal and to facilitate the subsequent detection of the pace pulses 40 at step 38.

Figure 3:
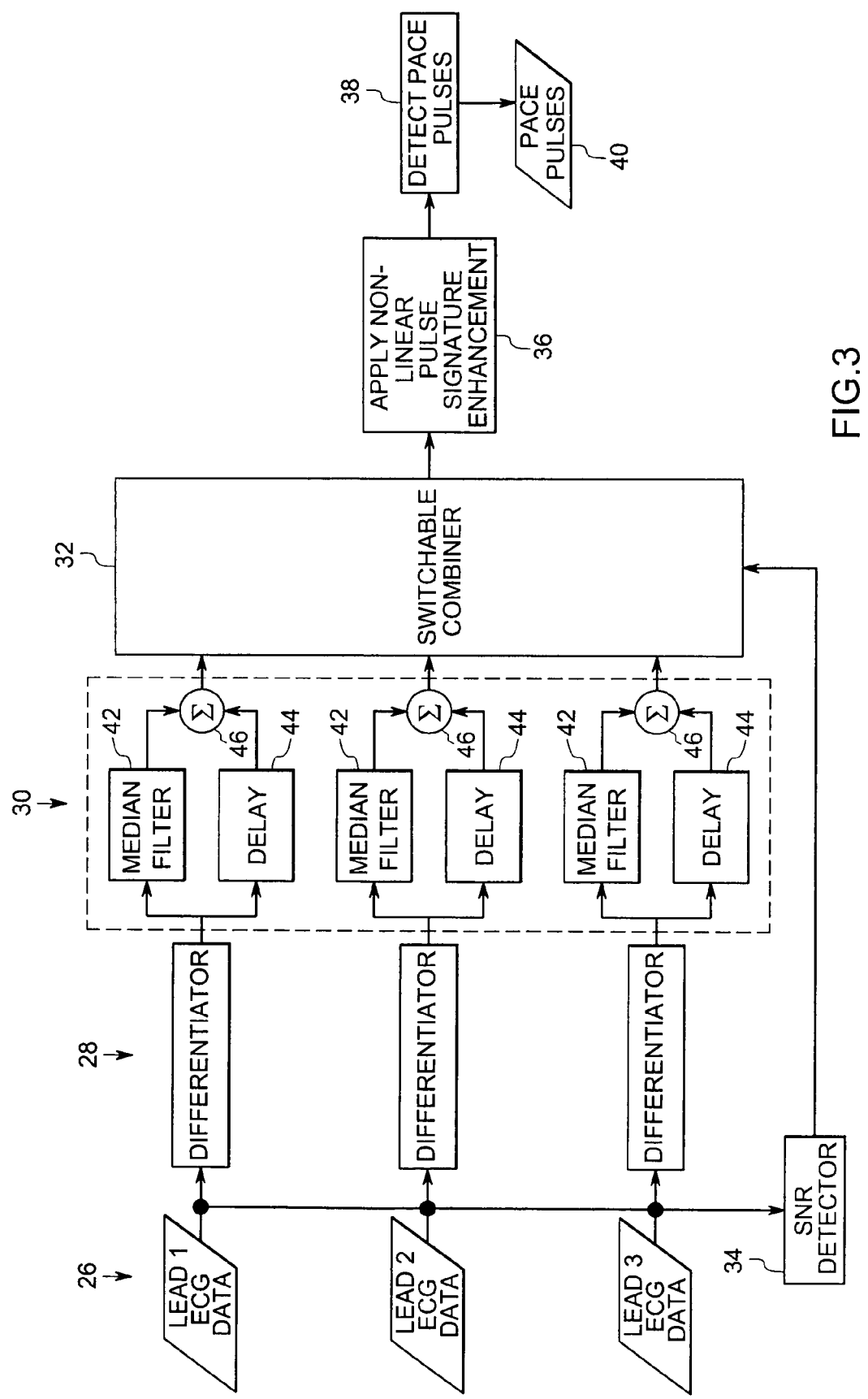
FIG. 3 is an exemplary embodiment of the method of enhancing pace pulses of FIG. 2.

The processing steps described hereinabove will be described in detail with reference to FIG. 3, wherein FIG. 3 illustrates an exemplary embodiment of the method illustrated in FIG. 2. In the embodiment of FIG. 3, each ECG data set 26 is processed via a differentiator or differentiation routine. For example, at step 28, the respective sets of ECG data 26 are differentiated to convert each pace pulse present within the ECG data 26 into a pair of impulses of opposite polarity, where each pair of differentiated pulses is separated by the generally constant width of the corresponding pulse. Differentiation may be accomplished via a simple first-order difference equation or by other techniques known in the art. In this example, if the input signal to the differentiator is represented as x(i), then the output of the differentiator, x'(i) may be represented as:

$$x'(i) = x(i) - x(i-1) \tag{1}$$

As a result of the differentiation process 28, superfluous low-frequency signals present in the ECG data 26 may be reduced or eliminated. For example, in the ECG data 26 that has undergone differentiation at step 28, the QRS complexes may be attenuated and baseline shifts due to respiration may be reduced or eliminated. Furthermore, after attenuation at step 28, extraneous noise, such as 60 Hz noise, in the ECG data 26 may be attenuated.

In the exemplary embodiment of FIG. 3, a filtration step 30 is performed subsequent to the differentiation step 28 to further enhance the pace pulses that may be present in the ECG data 26. For example, as illustrated in FIG. 3, in step 30, a filter, such as a median filter 42, may be applied to each respective ECG data set 26 to attenuate the plurality of pace pulses. In one embodiment, the median filter 42 may have an order in a range from about 9 to about 25. Processing the ECG data 26 via the median filter 42 typically results in the rejection of the plurality of pace pulses that may be present in the ECG data 26. Conversely, other signals, which do not constitute pace pulses, such as noise or other spurious signals, pass through the filtering process without modification. Therefore, the ECG data 26 is substantially free of pace pulses after application of the median filter 42, while maintaining other salient features of the ECG data 26.

Additionally, the ECG data 26 may also be processed via a delay unit 44, wherein a delay may be introduced to the ECG data 26 corresponding to the time delay introduced by median filter 42. Consequent to processing the ECG data 26 via the delay unit 44, a set of unfiltered ECG data that is synchronized with the corresponding filtered set of ECG data is generated. In the exemplary embodiment of FIG. 3, the filtered set of ECG data is subtracted from the corresponding synchronized set of unfiltered ECG data in a summation step 46 to generate an enhanced set of digital ECG data that includes one or more pace pulses but is generally free of the noise and spurious signals present in the filtered set of ECG data. In other words, the enhanced set of digital ECG data, due to the subtraction process, is relatively free of those features that were not filtered out of the filtered set of ECG data.

As may be noted in FIG. 3, the various steps described above are discussed and depicted as being performed on the respective ECG data sets 26 acquired from each respective lead 12 or other source. As depicted at step 32, the respective ECG data sets 26, after some or all of the processes described at steps 28 and 30 have been performed, may be combined at step 32 to generate a single signal representative of a combined set of ECG data. For example, in the exemplary embodiment of FIG. 3, the ECG data sets 26 are combined via a switchable combiner. As will be appreciated by one skilled in the art, the combiner may be employed when two or more sets of ECG data are available for processing.

In the depicted combining process it may be advantageous to retain the desired signals while attenuating noise. For example, aspects of the present technique employ a combining process that enhances correlated signals, such as pace pulses, while reducing uncorrelated signals, such as noise.

In such exemplary embodiments, information regarding the signal strength associated with the acquisition of each set of acquired ECG data is employed. For example, the signal strength may be represented by an average signal to noise ratio (SNR) value associated with the ECG data sets 26. The SNR detector 34 may be employed to determine an average value of the SNR on the plurality of leads. An algorithm for combining the plurality of ECG data sets 26 may be selected based upon the computed value of SNR such that the selected algorithm retains or enhances desired components of the signal and/or attenuates undesired components of the signal. The plurality of ECG data sets may be combined to generate a single set of combined ECG data using the selected algorithm.

For example, the SNR detector 34 may be employed to compute an approximate average SNR value that is associated with the sets of ECG data 26. A combinatorial method may then be selected based upon whether the SNR is above a given threshold value, between two thresholds values, and/or lower than a threshold value. For example, a "high" SNR having a SNR value above an upper threshold may result in the selection of a first combinatorial algorithm. Similarly, a "moderate" SNR having a SNR value between an upper and a lower threshold may result in the selection of a different combinatorial algorithm. However, a "low" SNR having a SNR value below a lower threshold may result in the selection of yet another combinatorial algorithm. Though two threshold values and three combinatorial algorithms are specified in this example, one of ordinary skill in the art will appreciate that other combinations are also possible. For example, a single threshold may be employed to select between two combinatorial algorithms or more than two threshold values may be employed to select from a greater number of combinatorial algorithms.

In one exemplary embodiment, the combination at step 32 may be selected for a high SNR value and may employ an optimal linear combination algorithm. For example, the combining algorithm may be accomplished in accordance with the equation:

$$c(i)=a_x x(i)+a_y y(i)+a_z z(i), \quad (2)$$

if the sum is greater than zero, where x(i), y(i) and z(i) represent the three input sets of ECG data 26 in the three-lead system depicted in FIG. 3 and where $a_x$, $a_y$ and $a_z$, represent the optimal lead gains, or $$c(i)=0 \quad (3)$$

if the sum is less than zero.

The optimal lead gains may be determined by a ratio of the pulse signal amplitude to the square of the root mean square (RMS) value of noise associated with the signal. As will be appreciated by one skilled in the art, the desired signals are correlated signals, while noise that may be present in the ECG data sets 26 are uncorrelated.

Figure 4:
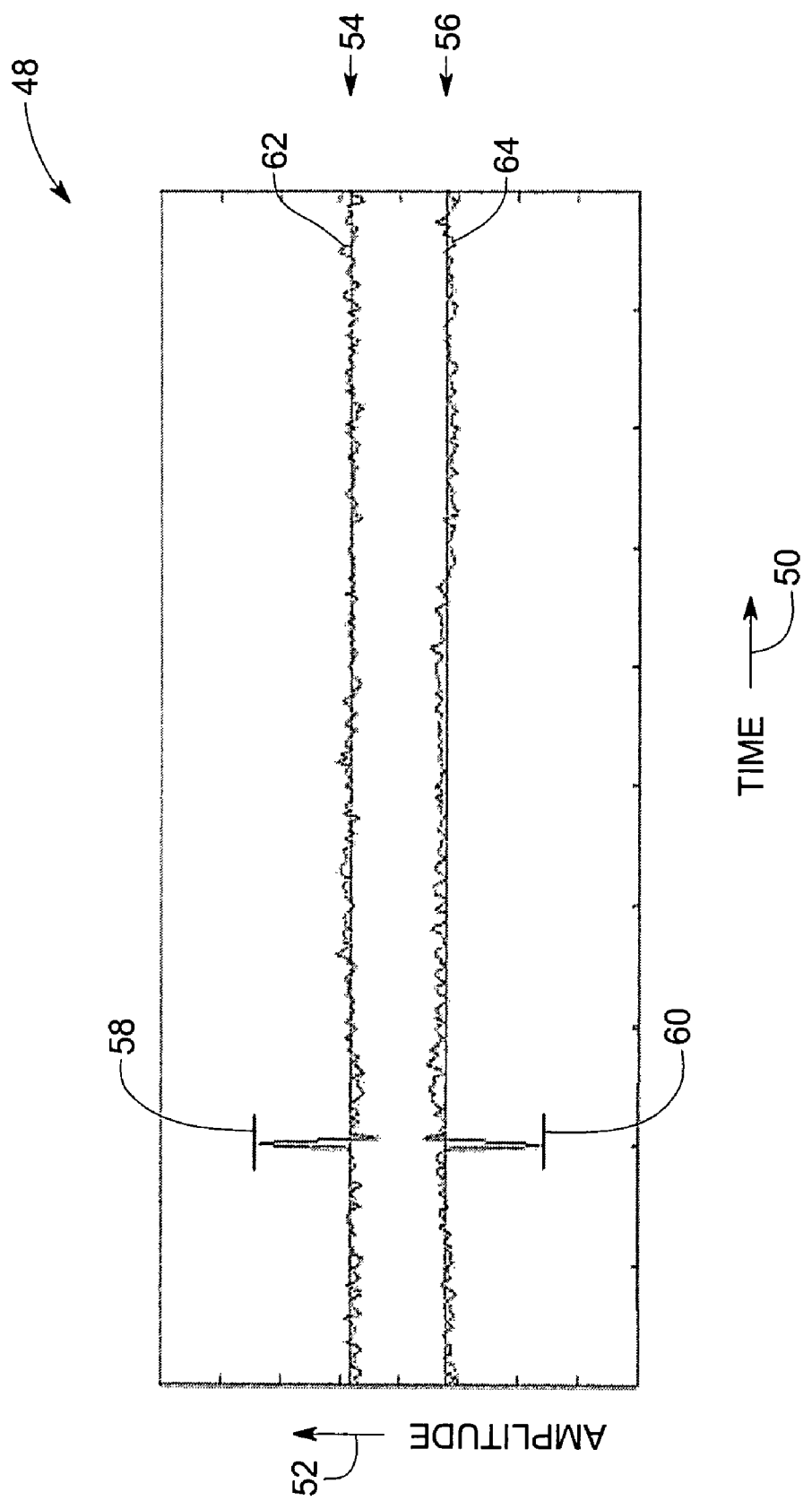
FIG. 4 illustrates a waveform generated during a simulated stress test performed in accordance with one aspect of the present technique.

The optimal lead gains may be computed as described hereinafter. FIG. 4 illustrates an ECG waveform 48 that may be representative of the ECG data set 26, wherein the signal amplitude 52 is plotted as a function of time 50. The total SNR associated with the sets of ECG data 26 may be maximized in accordance with the following equation:

$$SNR_{tot} = \frac{\sum_i a_i S_i}{\sqrt{\sum_i a_i^2 N_i^2}} = \frac{a_1 S_1 + a_2 S_2 + a_3 S_3}{\sqrt{a_1^2 N_1^2 + a_2^2 N_2^2 + a_3^2 N_3^2}} \quad (4)$$

where $S_i$ represents the signal energy for the $i^{th}$ ECG data set. The energy may be represented as:

$$S_i = A_i \quad (5)$$

where $A_i$ is the amplitude of the pace pulse for the $i^{th}$ ECG data set.

FIG. 4 shows an example using 2 sets of ECG data where $A_1$ 58 and $A_2$ 60 are representative of the signal amplitudes of a first signal 54 and a second signal 56, as illustrated in FIG. 4. $N_i$ may represent the noise energy for the $i^{th}$ ECG data set and is given by the following equation:

$$N_i = RMS_i$$

This is also illustrated in FIG. 4 where $RMS_1$ 62 and $RMS_2$ 64 are RMS values of the noise associated with the first signal 54 and the second signal 56 respectively. Finally, $a_i$ represents the weighting factor for the $i^{th}$ ECG data set. Typically, equation (4) may be solved for a set of $a_i$ values that maximize the total SNR.

The process of maximizing the total SNR for the weighted sum of input leads of equation (4) may be approximately equivalent to the process of minimizing a noise to signal ratio (NSR), which may be represented as follows:

$$NSR_{tot} = \frac{\sqrt{a_1 N_1^2 + a_2 N_2^2 + a_3 N_3^2}}{a_1 S_1 + a_2 S_2 + a_3 N_3} \quad (7)$$

Taking partial derivatives with respect to the weight factors $a_i$ and setting the result to zero:

$$\frac{\partial \left( \frac{\sqrt{\sum_i a_i N_i^2}}{\sum_i a_i S_i} \right)}{\partial a_i} = 0 \quad (8)$$

Let $$\Psi = \sum_i a_i N_i^2 \quad (9)$$

and $$\Phi = \sum_i a_i S_i \quad (10)$$

After taking the derivative of equation (7) as represented in equation (8) and substituting equations (9) and (10) in equation (8):

$$\frac{1}{\Phi} \frac{1}{2\sqrt{\Psi}} 2 a_i N_i^2 - \frac{\sqrt{\Psi}}{\Phi^2} S_i = 0 \quad (11)$$

Combining the fractions with a least common denominator (LCD):

$$\frac{a_i \Phi N_i^2 - S_i \Psi}{\Phi^2 \sqrt{\Psi}} = 0 \quad (12)$$

Equation (12) may be reduced to the following set of equations:

$$a_i = \frac{S_i \Psi}{N_i^2 \Phi} \quad (13)$$

where i=1, 2, 3, ... N, where N represents the number of leads 12.

Equation (13) represents a non-linear set of equations and may not have closed-form solutions. However, a solution set for equation (13) may be represented as:

$$a_i = \frac{S_i}{N_i^2} \quad (14)$$

Alternatively, in the case of single sample impulses, the signal component S may be represented by an amplitude of maximum magnitude, which may be of either polarity, wherein the polarity is positive or negative, attained within a frame that contains one or more impulses. It may be noted that the sign of the sample impulse having the amplitude of maximum magnitude be preserved in accordance with the combining algorithm. Furthermore, a noise component may be represented by a sum of the squared values of the remaining samples divided by the size of the frame. Hence, an optimal gain $a_x$ for the signal have single sample impulses may be represented as follows:

$$a_x = \frac{\operatorname{sign}(x_{max})|x_{max}|}{\frac{\sum_{j=1}^{N} x_i^2[j]}{N}} \quad (15)$$

In a similar fashion, in this exemplary embodiment, for moderate to high SNR values, a vector magnitude combiner may be employed to combine the plurality of input ECG data sets. The vector magnitude combiner may be represented by the following equation:

$$c(i) = \sqrt{x^2(i) + y^2(i) + z^2(i)} \quad (16)$$

where x(i), y(i) and z(i) represent the three input sets of ECG data 26 in the three-lead system depicted in FIG. 3.

Alternatively, in this exemplary embodiment, for low SNR signals, a non-linear combining algorithm may be employed to combine the sets of ECG data 26. For example, the following non-linear equation may be employed to combine the input sets of ECG data 26:

$$c(i) = \sqrt{|x(i)y(i)| + |x(i)z(i)| + |y(i)z(i)|} \quad (17)$$

where x(i), y(i) and z(i) represent the respective ECG data sets 26 in the three lead system depicted in FIG. 3.

In equation (17), the sum under the radical is a combination of the three individual leads multiplied two at a time. The cross-multiplication takes advantage of the significant correlation between the signal components on the three leads, thereby enhancing the pace signals. The cross-multiplication also beneficially facilitates the attenuation of uncorrelated impulsive noise that may otherwise be mistaken as pace pulses.

The result of the combinatorial step 32 is a single signal that includes the pace pulses. As will be appreciated by those of ordinary skill in the art, equations (2), (16) and (17) may be modified to accommodate different numbers of ECG data sets 26.

Subsequently, in the exemplary embodiment of FIG. 3, the single combined signal may be further processed to enhance the plurality of pace pulses that may be present in the combined signal. For example, the generally fixed width nature of the pace pulses may be employed to further enhance the pace pulse signals. In accordance with an exemplary embodiment of the present technique, at step 36, the combined signal of ECG data is processed using a non-linear pulse signature enhancer (NLPSE). In this embodiment, the input to the NLPSE is the combined ECG signal that includes pairs of impulses corresponding to each pace pulse, such as may be present after differentiation of the ECG data 26 at step 28. Application of the NLPSE at step 36 may enhance the dual impulses corresponding to each pace pulse, relative to other pulses that may be present, thereby, enhancing the pace pulses relative to non-pace pulse noise in the combined signal. For example, given an input c(i), which may represent an output of the combining step 32, the output y(i) of an exemplary NLPSE may be represented as:

$$y(i) = \sqrt{\sum_{k=0}^{L-1} |c(i+k)c(i-W+k)| - \sum_{j=1}^{W-L} |c(i-j)|^R} \quad (18)$$

if the value under the radical is greater than zero or $y(i)=0$ \quad (19)

if the value under the radical is less than zero.

In equation (18), W represents the average pulse width and L represents the pulse width of the differentiated pulse. Furthermore, the term $$\sum_{k=0}^{L-1} |c(i+k)c(i-W+k)|$$

may be referred to as a correlation term. Additionally, the term $$\sum_{j=1}^{W-L} |c(i-j)|^R$$

may represent the direct current (DC) rejection term with R representing the weighting factor for this term.

As may be inferred from equation (18), the NLPSE utilizes the dual impulse nature of the differentiated ECG data to enhance the dual impulse signature and reject single pulse interference. In particular, according to an exemplary embodiment of the present technique, the impulses in the combined signal of ECG data that are spaced at the average pulse width W, such as after differentiation at step 28, may be used to generate an output pulse of large amplitude via operation of the correlation term. For example, two impulses that are separated by a reference distance, W, which may represent a pulse width, may generate a large amplitude output pulse, in accordance with equation (18). Conversely, if the two impulses are not separated by the reference distance, W, the correlation term may be attenuated and no large amplitude output pulse results.

As may be appreciated by those of ordinary skill in the art, the DC rejection term of equation (18) may represent a penalty term, which will reduce the amplitude of the output if the signal level between the two differentiated pulses is not small. In other words, the NLPSE utilizes the DC rejection term to attenuate direct current (DC) and low frequency signals. In one exemplary embodiment, the weighting factor R is 1.8. In other embodiments of the present technique, the value of R may be in the range of 1 to 2. In addition, an absolute value of the DC rejection term, $c(i-j)$, may be considered in order to avert the erroneous weighting of the DC rejection term in equation (18).

As may be appreciated by those of ordinary skill in the art, application of the NLPSE to the ECG data 26, such as combined ECG data that has been differentiated and filtered, may enable the suppression of impulsive noise. In addition, spurious signals due to slowly varying signals of high-amplitude may be eliminated by application of the NLSPE. Therefore, an output of step 36 may be ECG data, which includes a pulse of large amplitude at the trailing edge of each pace pulse within the ECG data 26. As will be appreciated by one of ordinary skill in the art that the pre-processing module 16 (see FIG. 1) may employ some or all of the aspects of the technique discussed with regard to FIG. 3. For example, differentiation and non-linear pulse signature enhancement may be performed without performing filtration or SNR dependent combination. Similarly, either or both of the filtration and combination techniques discussed with regard to FIG. 3 may be performed without differentiation or non-linear signature enhancement as discussed above. The signal output by the pre-processing module 16 (see FIG. 1), regardless of which of the preceding aspects of the exemplary technique discussed above are performed, may be analyzed by the detection module 18 (see FIG. 1) to detect the enhanced pace pulses 40 (see FIG. 1). The detection process itself may consist of a threshold comparison between the pre-processor output signal and a threshold deemed to indicate the presence of a pace pulse 40.

Figure 5:
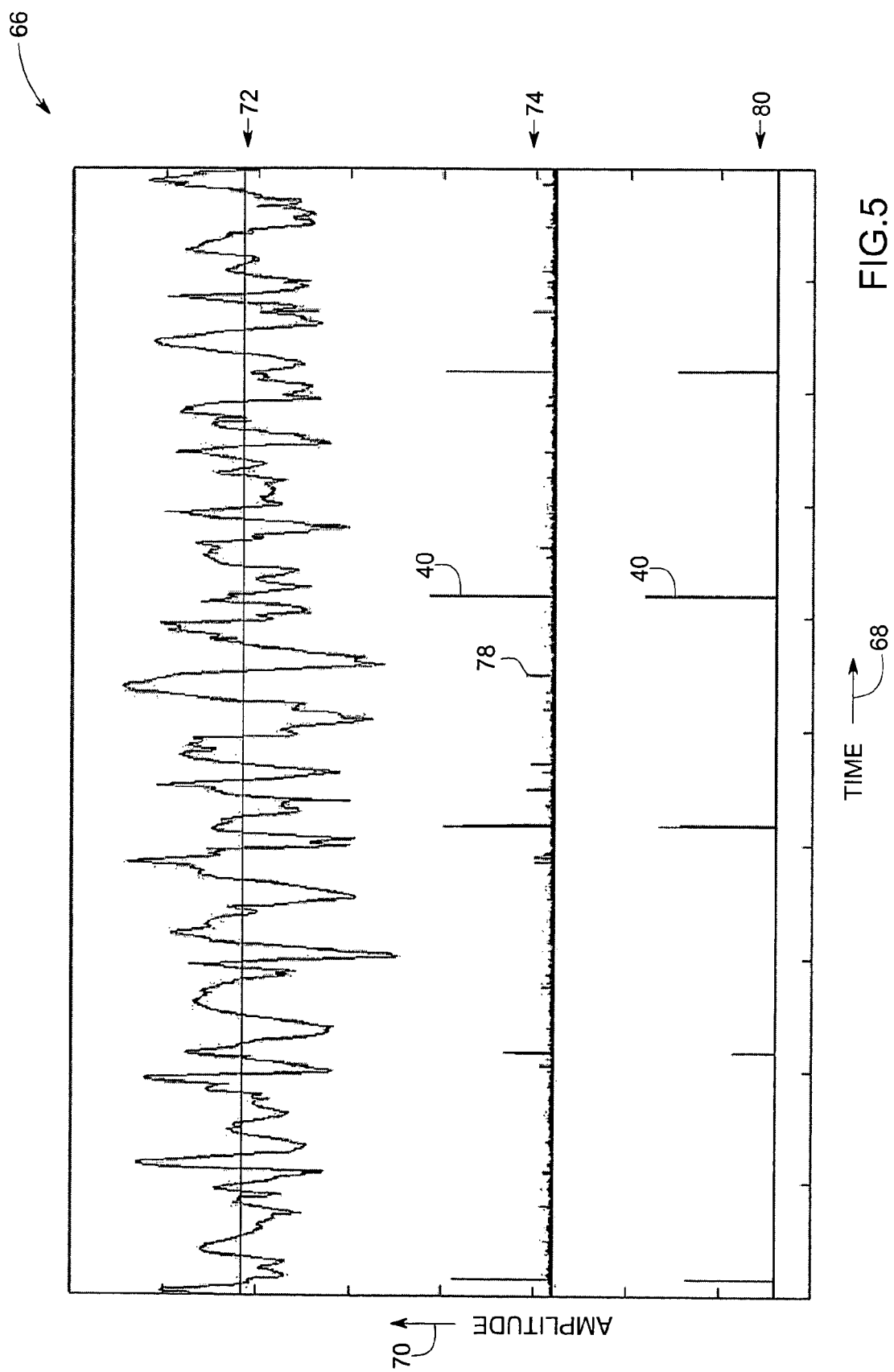
FIG. 5 illustrates input and output waveforms generated during a simulated stress test performing the steps depicted in FIG. 3.

Turning now to FIG. 5, exemplary input and output waveforms 66 generated during a simulated stress test are illustrated. In FIG. 5, the amplitudes 70 of the signals are plotted as a function of time 68. An input waveform 72, such as represented by an ECG data set 26 acquired via a lead 12, is illustrated. After processing the input waveform 72 via the steps 28, 30 and 32 discussed with regard to FIG. 3, a processed waveform 74 is generated. A plurality of pace pulses 40 may be observed in the processed waveform 74. However, the second waveform 74 may also include a noise component 78. After application of the non-linear pulse signature enhancement of step 36, the noise component may be substantially removed, resulting in an enhanced waveform 80. In the enhanced waveform 80, the pace pulses 40 are clearly visible, however the noise component 78 is substantially removed.

Once detected, the pace pulses 40 may be exhibited on a display unit, such as a printer 24 (see FIG. 1) or a display 22 (see FIG. 1) for review by a doctor or other medical professional. For example, the pace pulses 40 may be superimposed on an ECG trace displayed on a display 22 or on a printout generated by printer 24. Alternatively, the pace pulses 40 may be displayed as a second trace coinciding in time with an ECG trace.

The method for detecting and enhancing pace pulses described hereinabove advantageously enables the efficient detection of pace pulses 40 that may be present in the ECG data sets 26. The efficient detection of pace pulses 40 facilitates a diagnostician to evaluate the ECG data to determine if the heart is being actively paced. Furthermore, the method enables the efficient detection of pace pulses in a clinical ECG environment.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, such as C++ or JAVA. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

While only certain features of the invention have been illustrated and described herein, many modifications and changes will occur to those skilled in the art. In particular, though the present examples and discussions are directed to the detection of pacemaker pulses, one of ordinary skill in the art will appreciate that, the present techniques may be used in the general detection of rectangular pulses. It is, therefore, to be understood that the appended claims are intended to cover all such modifications and changes as fall within the true spirit of the invention.

The invention claimed is:

1. A method for enhancing pace pulses, the method comprising:
   providing a set of digital electrocardiogram data comprising a plurality of pulses, wherein each pulse is of a generally constant width;
   differentiating the plurality of pulses to generate a plurality of pairs of differentiated pulses, wherein each pair of differentiated pulses is separated by the generally constant width of the corresponding pulse,
   enhancing the plurality of pairs of differentiated pulses, wherein enhancing the plurality of pairs of differentiated pulses comprises applying a non-linear pulse signature enhancement algorithm configured to enhance pulses having a two-pulse, fixed-distance signature,
   generating a set of enhanced waveforms based on the non-linear pulse signature enhancement;
   wherein the plurality of pulses comprise a pace signal generated by a pacemaker to enhance pacing.

2. The method of claim 1, wherein the generally constant width comprises an average pulse width.

3. The method of claim 1, wherein enhancing the plurality of pairs of differentiated pulses comprises amplifying the amplitude of the plurality of pairs of differentiated pulses.

4. The method of claim 1, wherein enhancing the plurality of pairs of differentiated pulses comprises attenuating the amplitude of the other pulses.

5. The method of claim 1, wherein the algorithm comprises a correlation term configured to enhance a dual pulse signature.

6. The method of claim 1, wherein the algorithm comprises a correlation term configured to reject a single pulse signature.

7. The method of claim 1, wherein the algorithm comprises a rejection term configured to attenuate low-frequency signals.

8. The method of claim 1, wherein the algorithm comprises a correlation term and a rejection term.

9. The method of claim 1, comprising detecting a pacing signal from the set of enhanced waveforms.

10. The method of claim 9, comprising displaying the detected pacing signal on a display unit.

11. The method of claim 10, wherein displaying the detected pacing signal comprises superimposing the pacing signal on an electrocardiogram trace.

12. The method of claim 1, comprising enhancing the set of digital electrocardiogram data with a median filter.

13. A computer-readable medium comprising:
   code adapted to provide a set of digital electrocardiogram data comprising a plurality of pulses, wherein each pulse is of a generally constant width;
   code adapted to differentiate the plurality of pulses to generate a plurality of pairs of differentiated pulses, wherein each pair of differentiated pulses is separated by the generally constant width of the corresponding pulse; and
   code adapted to enhance the plurality pairs of differentiated pulses by apply a non-linear pulse signature enhancement algorithm configured to enhance pulses having a two-pulse, fixed-distance signature, wherein the code adapted to enhance the plurality of pairs of differentiated pulses comprises amplifying the amplitude of the plurality of pairs of differentiated pulses and attenuating the amplitude of the other pulses;
   code adapted to generate a set of enhanced waveforms based on the non-linear pulse signature enhancement wherein the plurality of pulses comprise a pace signal generated by a pacemaker to enhance pacing.

14. The computer-readable medium, as recited in claim 13, comprising code adapted to detect a pacing signal from the set of enhanced waveforms.

15. The computer-readable medium, as recited in claim 13, comprising code adapted to display the detected pacing signal on a display unit.

16. The computer-readable medium, as recited in claim 13, comprising code adapted to enhance the set of digital electrocardiogram data with a median filter.

17. A method for enhancing pace pulses, the method comprising:
   providing digital electrocardiogram data comprising a plurality of pace pulses;
   attenuating the plurality of pace pulses in the digital electrocardiogram data to generate a filtered set of the digital electrocardiogram data;
   subtracting the filtered set from a corresponding synchronized unfiltered set of the digital electrocardiogram data to generate a processed set of the digital electrocardiogram data; and
   applying a non-linear pulse signature enhancement to the processed set of the digital electrocardiogram data;
   generating a set of enhanced waveforms based on the non-linear pulse signature enhancement wherein the plurality of pulses comprise a pace signal generated by a pacemaker to enhance pacing.

18. The method of claim 17, wherein attenuating the plurality of pace pulses comprises applying a median filter to the digital electrocardiogram data.

19. The method of claim 17, wherein attenuating the plurality of pace pulses comprises removing the plurality of pace pulses.

20. The method of claim 17, wherein the corresponding synchronized unfiltered set of the digital electrocardiogram data is generated by introducing a delay to the digital electrocardiogram data corresponding to the time delay introduced by the filter.

21. The method of claim 17, comprising detecting a pacing signal from the enhanced waveforms.

22. The method of claim 17, comprising processing the digital electrocardiogram data with a differentiator.

23. The method of claim 17, wherein the plurality of pace pulses comprises a differentiated pace signal.

24. The method of claim 17, wherein the plurality of pace pulses comprises a pace signal generated by a pacemaker.

25. The method of claim 17, comprising displaying the detected pace signal on a display unit.

26. The method of claim 25, wherein displaying the detected pacing signal comprises superimposing the pace pulses on an electrocardiogram trace.

27. A computer-readable medium comprising:
   code adapted to provide digital electrocardiogram data comprising a plurality of pace pulses;
   code adapted to attenuate the plurality of pace pulses in the digital electrocardiogram data to generate a filtered set of the digital electrocardiogram data;
   code adapted to subtract the filtered set from a corresponding synchronized unfiltered set of the digital electrocardiogram data to generate a processed set of the digital electrocardiogram data; and
   code adapted to apply a non-linear pulse signature enhancement to the processed set of the digital electrocardiogram data;
   code adapted to generate a set of enhanced waveforms based on the non-linear pulse signature enhancement wherein the plurality of pulses comprise a pace signal generated by a pacemaker to enhance pacing.

28. The computer-readable medium, as recited in claim 27, wherein code adapted to attenuate the plurality of pace pulses comprises applying a median filter to the digital electrocardiogram data.

29. The computer-readable medium, as recited in claim 27, wherein code adapted to, attenuate the plurality of pace pulses comprises removing the plurality of pace pulses.

30. The computer-readable medium, as recited in claim 27, wherein code adapted to subtract the filtered set from a corresponding synchronized unfiltered comprises code adapted to generate the corresponding synchronized unfiltered set of the digital electrocardiogram data by introducing a delay to the digital electrocardiogram data corresponding to the time delay introduced by the filter.

31. The computer-readable medium, as recited in claim 27 comprising code adapted to detect a pacing signal from the enhanced waveforms.

32. The computer-readable medium, as recited in claim 27, comprising code adapted to process the digital electrocardiogram data with a differentiator.

33. The computer-readable medium, as recited in claim 27, comprising code adapted to display the detected pace signal on a display unit.

34. The computer-readable medium, as recited in claim 33, wherein code adapted to display the detected pacing signal comprises superimposing the pace pulses on an electrocardiogram trace.

35. A method for combining signals, the method comprising:
- providing a plurality of sets of digital electrocardiogram data;
- measuring a signal strength of the plurality of sets of digital electrocardiogram data;
- combining the plurality of sets of digital electrocardiogram data based on the signal strength to generate a combined single set of digital electrocardiogram data; and
- applying a non-linear pulse signature enhancement to the combined set of the digital electrocardiogram data;
- generating a set of enhanced waveforms based on the non-linear pulse signature enhancement to assist in detecting an underlying heart condition.

36. The method of claim 35, wherein the signal strength comprises a signal to noise ratio.

37. The method of claim 35, wherein combining the plurality of sets of digital electrocardiogram data based on the signal strength comprises selecting an algorithm based upon the signal strength and combining the plurality of sets of digital electrocardiogram data using the algorithm.

38. The method of claim 37, wherein combining the plurality of sets of digital electrocardiogram data comprises applying a weighting factor to each of the plurality of sets of digital electrocardiogram data, and wherein the weighting factor is estimated by a ratio of pulse amplitude to the square of the root means square value of noise.

39. The method of claim 37, wherein the combining the plurality of sets of digital electrocardiogram data comprises applying a multiplicative combining technique.

40. The method of claim 39, wherein applying the multiplicative combining technique to three or more sets of digital electrocardiogram data comprises multiplicatively combining two leads at a time and summing the multiplicative combinations.

41. The method of claim 35, comprising detecting a pacing signal from the single set of the digital electrocardiogram data.

42. The method of claim 35, comprising processing the plurality of sets of digital electrocardiogram data with a differentiator.

43. The method of claim 35, comprising enhancing the plurality of sets of digital electrocardiogram data with a median filter.

44. A computer-readable medium comprising:
- code adapted to provide a plurality of sets of digital electrocardiogram data;
- code adapted to measuring a signal strength of the plurality of sets of digital electrocardiogram data;
- code adapted to combining the plurality of sets of digital electrocardiogram data based on the signal strength to generate a combined single set of digital electrocardiogram data; and
- code adapted to apply a non-linear pulse signature enhancement to the combined set of the digital electrocardiogram data;
- code adapted to generate a set of enhanced waveforms based on the non-linear pulse signature enhancement to assist in detecting an underlying heart condition.

45. The computer-readable medium, as recited in claim 44, wherein code adapted to measuring a signal strength comprises measuring a signal to noise ratio.

46. The computer-readable medium, as recited in claim 44, wherein code adapted to combine the plurality of sets of digital electrocardiogram data based on the signal strength comprises selecting an algorithm based upon the signal strength and combining the plurality of sets of digital electrocardiogram data using the algorithm.

47. The computer-readable medium, as recited in claim 46, wherein the code adapted to combine the plurality of sets of digital electrocardiogram data comprises applying a weighting factor to each of the plurality of sets of digital electrocardiogram data, and wherein the weighting factor is estimated by a ratio of pulse amplitude and the root means square value of noise.

48. The computer-readable medium, as recited in claim 46, where code adapted to combine the plurality of sets of digital electrocardiogram data comprises applying a multiplicative combining technique.

49. The computer-readable medium, as recited in claim 48, where code adapted to apply the multiplicative combining technique to three or more sets of digital electrocardiogram data comprises multiplicatively combining two leads at a time and summing the multiplicative combinations.

50. The computer-readable medium, as recited in claim 44, comprising code adapted to detect a pacing signal from the single set of the digital electrocardiogram data.

51. The computer-readable medium, as recited in claim 44, comprising code adapted to process the plurality of sets of digital electrocardiogram data with a differentiator.

52. The computer-readable medium, as recited in claim 44, comprising code adapted to enhance the plurality of sets of digital electrocardiogram data with a median filter.

53. A method for combining signals, the method comprising:
- providing a plurality of sets of digital electrocardiogram data;
- measuring a signal strength of the plurality of sets of digital electrocardiogram data; selecting an algorithm based upon the signal strength; and
- combining the plurality of sets of digital electrocardiogram data using the algorithm, wherein the algorithm applies a weighting factor to each of the plurality of sets of digital electrocardiogram data and wherein the weighting factor is estimated by a ratio of pulse amplitude to the square of the root means square value of noise;
- generating a combined single set of digital electrocardiogram data to assist in detecting an underlying heart condition.

54. The method of claim 53, wherein the signal strength comprises a signal to noise ratio.

55. The method of claim 53, wherein the combining the plurality of sets of digital electrocardiogram data comprises applying a multiplicative combining technique.

56. The method of claim 55, wherein applying the multiplicative combining technique to three or more sets of digital electrocardiogram data comprises multiplicatively combining two leads at a time and summing the multiplicative combinations.

57. The method of claim 53, comprising detecting a pacing signal from the single set of the digital electrocardiogram data.

58. The method of claim 53, comprising processing the plurality of sets of digital electrocardiogram data with a differentiator.

59. The method of claim 53, comprising enhancing the plurality of sets of digital electrocardiogram data with a median filter.

60. A computer-readable medium comprising:
- code adapted to provide a plurality of sets of digital electrocardiogram data;

code adapted to measuring a signal strength of the plurality of sets of digital electrocardiogram data;

code adapted to select an algorithm based upon the signal strength; and code adapted to combine the plurality of sets of digital electrocardiogram data using the algorithm, wherein the algorithm applies a weighting factor to each of the plurality of sets of digital electrocardiogram data and wherein the weighting factor is estimated by a ratio of pulse amplitude and the root means square value of noise;

code adapted to generate a combined single set of digital electrocardiogram data to assist in detecting an underlying heart condition.

61. The computer-readable medium, as recited in claim 60, wherein code adapted to measuring a signal strength comprises measuring a signal to noise ratio.

62. The computer-readable medium, as recited in claim 60, where code adapted to combine the plurality of sets of digital electrocardiogram data comprises applying a multiplicative combining technique.

63. The computer-readable medium, as recited in claim 62, where code adapted to apply the multiplicative combining technique to three or more sets of digital electrocardiogram data comprises multiplicatively combining two leads at a time and summing the multiplicative combinations.

64. The computer-readable medium, as recited in claim 60, comprising code adapted to detect a pacing signal from the single set of the digital electrocardiogram data.

65. The computer-readable medium, as recited in claim 60, comprising code adapted to process the plurality of sets of digital electrocardiogram data with a differentiator.

66. The computer-readable medium, as recited in claim 60, comprising code adapted to enhance the plurality of sets of digital electrocardiogram data with a median filter.

* * * * *